United States Patent [19]

Bagby

[11] Patent Number: 4,501,269
[45] Date of Patent: Feb. 26, 1985

[54] PROCESS FOR FUSING BONE JOINTS

[75] Inventor: George W. Bagby, Spokane, Wash.

[73] Assignee: Washington State University Research Foundation, Inc., Pullman, Wash.

[21] Appl. No.: 581,841

[22] Filed: Feb. 21, 1984

Related U.S. Application Data

[63] Continuation-in-part of Ser. No. 330,169, Dec. 11, 1981, abandoned.

[51] Int. Cl.³ ............................................... A61F 5/04
[52] U.S. Cl. ................................ 128/92 G; 128/92 C; 3/1; 3/1.9
[58] Field of Search ............. 128/92 G, 92 CA, 92 C, 128/92 B, 92 BA; 3/1, 1 G, 1 GI

[56] References Cited

U.S. PATENT DOCUMENTS

| 3,112,743 | 12/1963 | Cochran et al. | 128/92 C |
| 3,228,393 | 1/1966 | Michele | 128/92 CA |
| 3,849,805 | 11/1974 | Leake et al. | 3/1 G |

OTHER PUBLICATIONS

"Methods of Lumbar Fusion" by Norman W. Hoover, Journal of Bone and Joint Surgery, vol. 50-A, No. 1, Jan., 1968, pp. 194–210.
Editorial Comment by Gary E. Friedlaender, Clinical Orthopaedics and Related Research, No. 174, Apr. 1983, pp. 2–4.
"Wobbler Syndrome in Horses", by Geo. W. Bagby, Spokane County Medical Society Bulletin, Spring Issue, 1979, pp. 27 and 45.
Scorecard—"Stable Stable", Sports Illustrated, May 21, 1979, p. 15.
"WSU Clinic Helps Asia Ruler Conquer Wobbler's Disease", Daily Racing Form (Seattle, WA) Mar. 25, 1979.

Primary Examiner—Richard J. Apley
Assistant Examiner—David Isabella
Attorney, Agent, or Firm—Wells, St. John & Roberts

[57] ABSTRACT

A process for immediate stabilization and subsequent promotion of bone-to-bone fusion in a joint where separation of the bones is restricted by surrounding ligaments or other soft tissue. A hole is bored transversely across the joint. A slightly larger cylindrical basket is driven into the hole, thereby spreading the bones in resistance to the tensile forces of the surrounding tissue. Immediate stabilization of the joint is achieved by the implantation of the rigid cylindrical basket. Subsequent bone-to-bone fusion is achieved, both through and about the basket, which is filled with bone fragments produced during the boring step.

3 Claims, 11 Drawing Figures

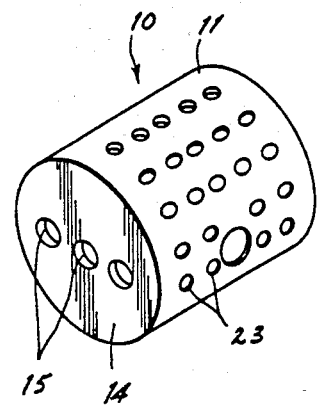
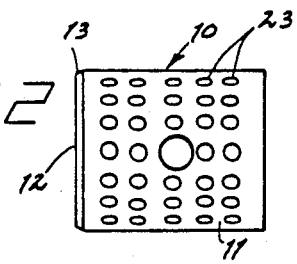
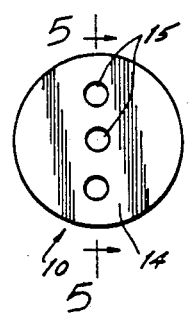
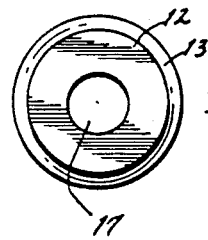
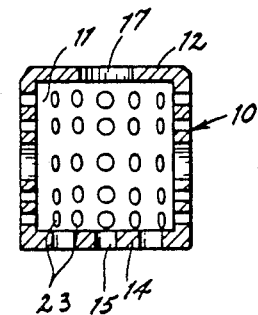
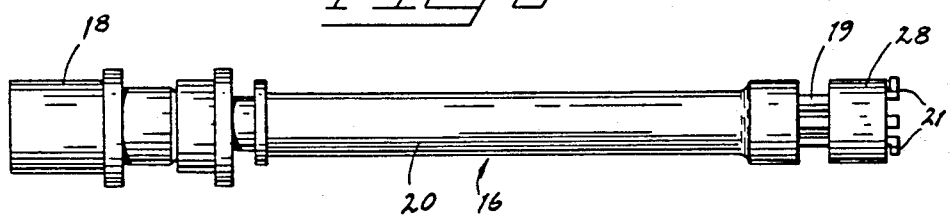

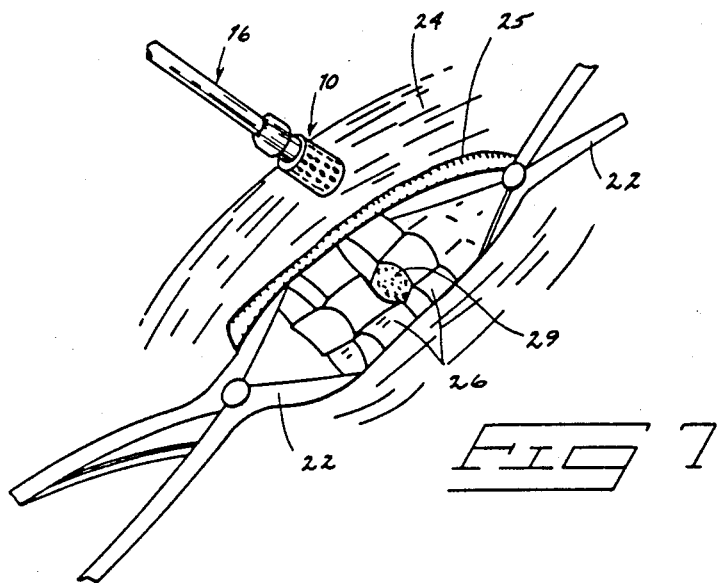
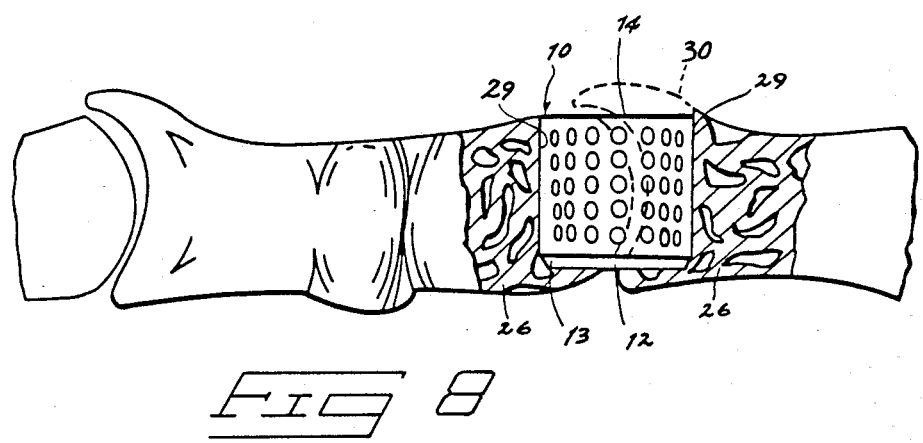

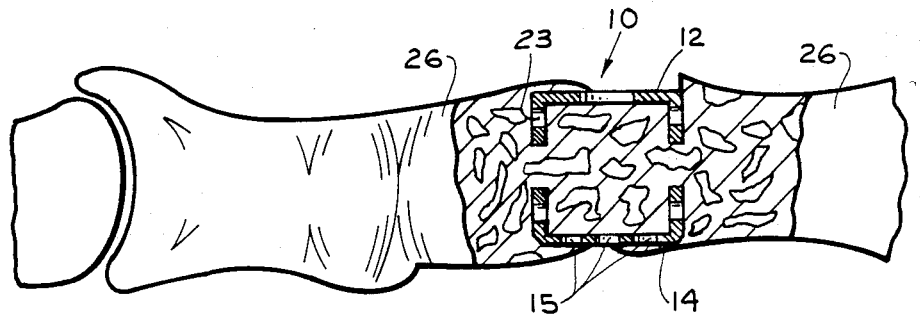
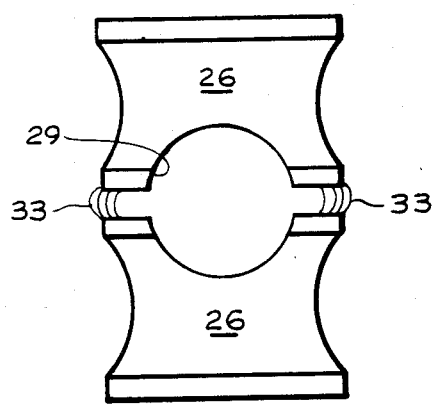 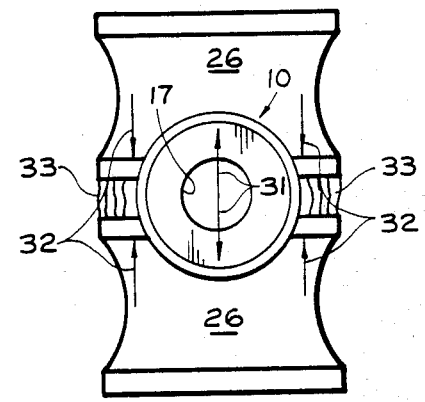

PROCESS FOR FUSING BONE JOINTS

RELATED APPLICATIONS

This is a continuation-in-part of copending application Ser. No. 330,169, filed Dec. 11, 1981 and titled "Bone Graft Cage", now abandoned.

FIELD OF THE INVENTION

This disclosure relates to a surgical procedure for fusing a bone joint formed by opposed bony surfaces surrounded by ligaments which resist expansion of the joint.

BACKGROUND OF THE INVENTION

This invention was developed specifically for the correction of Wobbler syndrome in horses, which is a form of progressive ataxia due to instability of the cervical spine creating encroachment on the spinal cord (equine cervical vertebral malformation). Earlier attempts by the inventor to surgically stabilize the spine in horses utilized placement of a precut bone dowel within a prepared hole centered over the disk and partially cut into the vertebral end plates both above and below the disk. A discussion of these attempts was published in the 1979 Spring Issue of the *Spokane County Medical Society Bulletin*.

One difficulty posed by this earlier work related to the inherent biological problems in using allografts (tissues transplanted between individuals that are members of the same species but are not genetically identical) or xenografts (tissues transferred between different species). While the fusion technique using dowels has been successfully applied to humans by using bone taken from a remote area of the body, this is impractical when the technique is applied to horses. Removal of bone from the leg of a horse, as an example, would seriously affect the running ability of the horse. In addition, in all applications, dowels produced as autografts (tissues transplanted from one site to another site in the same individual) involve two separate surgical operations, with resulting increases in the likelihood of complications.

It is well known that autogenous tissues are considered to be the most biologically suitable graft material. Histocompatibility differences between donor and recipient do not exist, and there is no possibility of transmitting disease from one individual to another. The potential disadvantages of autografts include the need to sacrifice normal structures elsewhere in the body, morbidity associated with a second surgical site or extended primary incision, and limitations in the size, shape, and quality of available autogenous tissues.

The instant method of bone-to-bone fusion not only immediately stabilizes the joint, as does the dowel technique when successful, but also promotes bone growth across the joint by use of readily available autogenous tissue in the form of bone fragments removed during preparation of the joint. No additional surgery or bone removal is required. This invention further answers the need for perfect cylindrical bone dowels implant, which are impossible to meet when using natural bone.

DESCRIPTION OF THE DRAWINGS

A preferred embodiment of the invention is illustrated in the accompanying drawings, in which:

FIG. 1 is an exploded isometric view of the bone basket;
FIG. 2 is a side view;
FIG. 3 is an end view;
FIG. 4 is an opposite end view;
FIG. 5 is a sectional view taken along line 5—5 in FIG. 3;
FIG. 6 is a side view of an implanting tool;
FIG. 7 is an illustration of the implanting step;
FIG. 8 is a partial sectional view of a spine, showing the implanted bone basket;
FIG. 9 is a view similar to FIG. 8, illustrating bone-to-bone fusion following implantation of the bone basket;
FIG. 10 is a diagrammatic view illustrating the boring step of the process; and
FIG. 11 is a diagrammatic view illustrating stabilization of the joint after implanting the bone basket.

DESCRIPTION OF THE PREFERRED EMBODIMENT

In compliance with the constitutional purpose of the Patent Laws "to promote the progress of science and useful arts" (Article 1, Section 8), applicant submits the following disclosure of the invention.

The process described below is applicable to any human or animal joint formed by opposed contiguous bony surfaces which are covered and separated by intervening cartilage and are surrounded by ligaments which resist expansion of the joint. Specific examples of such joints are a spinal joint between adjacent vertebrae or the ankle joint. The process was developed to immediately stabilize the joint and to further promote ultimate bone-to-bone fusion. It eliminates the need for the additional surgery previously required to utilize autogenous bone grafts or dowels. It provides a strong, rigid cylinder for implantation in a transverse position centered across a joint. The implanted structure is in the form of a perforated cylindrical bone basket which can be filled with bone fragments produced during the preparation of the joint. These bone fragments provide autogenous tissue to promote bone growth through the basket, as well as around it.

The process involves the initial steps of surgically accessing the joint and removing intervening cartilage located between the contiguous bony surfaces. A transverse cylindrical opening is then bored across the contiguous bony surfaces. Immediate stabilization is achieved by driving into the cylindrical opening a hollow basket having a rigid perforated cylindrical wall whose outside diameter is slightly greater than the inside diameter of the cylindrical opening. The implanting of the basket spreads the bony surfaces apart in opposition to the resistance to expansion of the joint provided by the surrounding ligaments. The basket is subsequently filled with bone fragments produced by the boring step. The bone fragments located within the basket promote bone growth about the basket and through its perforated cylindrical wall while the joint is maintained in a stabilized condition by the implanted basket. The surgical procedure is completed by closing the wound. The basket remains permanently within the fused joint and no secondary surgical procedure is required to later remove it.

The rigid basket implant provides immediate and prolonged stability the joint and serves as a matrix for bony fusion across the joint area. The controllable size, shape and strength of the rigid basket makes surgical implantation more efficient and the results more predictable. The implant, which is slightly larger than the implant hole, provides expansion-compression of the joint, in contrast to direct compression for implants used for arthrodesis and fracture treatment. Expansion-compression is limited to special anatomical regions where separation of the bones is restricted by soft tissue structures. The vertebrae are good examples of such joint structure, since the annulus fibrosus of the disk functions to limit the amount of bony distraction.

By implanting a cylindrical rigid basket between prepared contiguous bony surfaces across a joint, immediate stability of the joint can be achieved. The underlying principle is one of expansion-compression (or distraction-compression). The expansion occurs due to the slightly greater diameter of the cylindrical basket in relation to the diameter of the hole within which it is implanted. The compression occurs due to the tensioning of the surrounding ligaments attached to the bones forming the joint. The basket is held in place between the bones by the compressive forces exerted on the bones (and basket) by the ligaments which resist expansion of the joint. The basket takes up all slack in the surrounding ligaments created by the decreased thickness of the intervening cartilage (disk) which creates the problem being corrected.

The basket 10 includes a rigid perforated cylindrical wall 11. The basket might be made of stainless steel or other material suitable for implantation purposes. Its cylindrical wall 11 must have greater compressive strength than the bone structure into which it is implanted.

A first end 12 of the cylindrical wall 11 includes a beveled outer surface 13 to facilitate its insertion between the contiguous bony surfaces of the joint. A threaded circular end cap at the end 12 has an open central aperture 17 formed through it, providing limited access to the interior of the basket 10. The opposite end 14 of the basket 10 is substantially closed, and has three apertures 15 formed through it for cooperation with an installing tool discussed below.

The cylindrical wall 11 is provided with a continuous array of perforations formed through it. These perforations are indicated generally by the reference numeral 23. They can be of varying sizes. It has been found particularly useful to include a pair of diametrically opposed enlarged openings through the wall 11 which can be aligned across the joint to permit an enlarged bone ingrowth structure in alignment with the joint (see FIG. 9).

The installing tool 16 shown in FIGS. 6 and 7 includes an outer end 18 and a connecting shaft 19 leading to a basket support 28 having inwardly movable prongs 21 adapted to releasably fit within the apertures 15 formed through end 14 of the basket. Shaft 19 is surrounded by a slidable cylinder 20.

FIg. 7 generally illustrates implantation of the basket 10 between adjacent vertebrae. After first anesthetizing the patient, an incision is made to surgically access the location of the joint. As shown, the incision is made through the skin surfaces 24 as indicated by numeral 25. The surrounding tissues are held apart from the operational area by conventional clamps 22.

The first step in preparing the joint for implantation is the boring of a cylindrical opening centered across the contiguous bony surfaces of the joint. The hole 29 is bored between two adjacent vertebrae 26. Before boring the hole, it is necessary to remove any intervening cartilage located between the contiguous bony surfaces.

As schematically shown in FIG. 10, the hole 29 is positioned across the transverse center of the joint. The cylindrical opening is defined by opposing semi-cylindrical inner surfaces produced across the opposed bones at the joint. The hole can be bored by conventional surgical tools. As indicated at 30 (FIG. 8), bony extensions in the intended path of the hole must be removed during the boring step.

The diameter of the hole 29 is selected to be slightly smaller than the diameter of the basket 10. As an example, the cylindrical inside diameter of hole 29 might be approximately two millimeters less than the cylindrical outside diameter of basket 10. The diameter difference should be chosen to match the physical dimensions of the specific joint being fused. More particularly, this difference should be chosen so as to assure that the joint expansion achieved by implantation of the basket will fully take up all slack in the surrounding ligaments that resist joint expansion.

The bone chips that are produced during the boring of the hole 29 are retained for later filling of the basket 10. Basket 10 can be filled with bone chips prior to its insertion. By providing basket 10 with a threadably removable end cover at 14, one can alternately fill the basket after its implantation between the bones of the joint.

After preparation of hole 29, basket 10 is attached to the installing tool 16 by attaching the prongs 21 within the complementary apertures 15. The basket 10 is driven between the bones in the prepared joint. Its tapered end surfaces 13 assist in centering the basket coaxially within hole 29 and wedge the two bones slightly apart as the basket is driven between them.

As is evident in FIG. 8, the axial length of the basket 10 is selected so as to be substantially equal to the transverse width of the joint across which the opening 29 is bored. The outer ends of the basket 10 should not protrude beyond the surrounding bone.

After initially positioning the basket in hole 29, it is implanted by impacting the outer end 18 of the installing tool 16. Impact forces can be provided by engagement with a hammer, mallet or any equivalent device.

After installation of the basket 10, the installing tool 16 is detached. In the specific embodiment shown, the prongs 21 are compressed and released from the receiving apertures 15 by sliding cylinder 20 toward the joint. The surgical process is then completed by removing clamps 22 and closing the incision 25.

One significant advantage of this procedure, when compared to other fusion techniques, is that the adjacent bones are immediately stabilized and the joint is maintained in an immobile condition. Stabilization occurs, as shown schematically in FIG. 11, due to the joint expansion that results from implanting within the hole 29 a cylinder having a slightly larger diameter. The resilience of the bone structure permits the interior surfaces of the cylindrical opening to spread slightly to accommodate the difference in diameter of the basket. However, the diameter difference occurring longitudinally through the joint, which tends to spread the two bones apart, is resisted by the strong, tough and basically inextensile nature of the surrounding ligaments attached to the bone, schematically illustrated by the attached annulas fibrosis 33. Since these ligaments do not readily yield, they oppose the physical expansion of the joint. The resulting expansion/contraction forces are concentrated through the axial center of the basket, as indicated by arrows 31 in FIG. 11. The reaction forces exerted on the vertebrae 26 due to the strength and rigidity of the cylindrical wall 11 about basket 10 are balanced by tensile forces (arrows 32) in the surrounding ligaments.

Permanent fusion of the bones at the joint occurs due to the promotion of osteogenesis by ingrowth of bone tissue through and about the basket 10. The expansive/compressive forces exerted on the bones by implanting of basket 10 encourages bone healing and growth by applying physical load to the live bone cells. The provision of bone fragments or chips within basket 10 further encourages bone ingrowth and eventual fusion, as shown in FIG. 9. The basket serves as a matrix for fusion across the joint, and is permanently embedded within the resulting bone structure as a physical reinforcement. The permanent interlocking of the bone and basket, which results due to its perforated structure, provides a permanently fused joint in areas such as the spine, where immobilization of the joint for fusion is otherwise very difficult to achieve.

This procedure can be applied to any anatomical joint region where separation of the contiguous bone surfaces is restricted by surrounding soft tissue structures, such as ligaments. The vertebrae are good examples, since the annulus fibrosus of the disk functions to limit the amount of bony distraction. Another example of a suitable joint is the ankle.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

I claim:

1. A process for stabilizing and promoting bone-to-bone fusion of a human or animal joint such as a spinal joint between adjacent vertebrae or the ankle joint formed by opposed contiguous bony surfaces which are covered and separated by intervening cartilage and are surrounded by ligaments which resist expansion of the joint; comprising the following steps:

surgically accessing the joint;

removing intervening cartilage located between the contiguous bony surfaces;

boring across the contiguous bony surfaces a transverse cylindrical opening having a selected inside diameter about opposed semi-cylindrical surface areas formed across the respective bony surfaces;

retaining the fresh autogenous bone fragments produced by the boring step;

driving into the transverse cylindrical opening a hollow basket having a rigid perforated cylindrical wall whose outside diameter is slightly greater than the inside diameter of the cylindrical opening to immediately stabilize the joint by spreading the bony surfaces apart in opposition to the resistance to expansion of the joint provided by the surrounding ligaments;

filling said hollow basket with fresh autogenous bone fragments produced by the boring step, thereby omitting the need for a second surgical site, to promote bone ingrowth about the basket and through its perforated cylindrical wall while providing immediate stabilization of the joint; and closing the access to the joint.

2. A process for stabilizing and promoting fusion of a human or animal joint as claimed in claim 1, further comprising the following steps:

attaching an implant tool to the bone cage before driving it into the cylindrical opening;

applying impact to an end of the tool to drive the bone cage within the cylindrical opening; and removing the tool from the bone cage after driving the bone cage into the cylindrical opening.

3. A process for stabilizing and promoting fusion of a human or animal joint as claimed in claim 1, wherein the difference in diameter between the inside diameter of the cylindrical opening and the outside diameter of the bone cage is approximately two millimeters.

* * * * *